(12) United States Patent  (10) Patent No.: US 7,063,719 B2
Jansen et al.  (45) Date of Patent: *Jun. 20, 2006

(54) STENT DEVICES WITH DETACHABLE DISTAL OR PROXIMAL WIRES

(75) Inventors: Lex P. Jansen, Pleasanton, CA (US); Henry Nita, Redwood Shores, CA (US); John E. Ortiz, East Palo Alto, CA (US)

(73) Assignee: Boston Scientific SciMed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/423,369

(22) Filed: Apr. 25, 2003

(65) Prior Publication Data

US 2003/0199965 A1    Oct. 23, 2003

Related U.S. Application Data

(63) Continuation of application No. 09/724,731, filed on Nov. 28, 2000, now Pat. No. 6,579,308.

(51) Int. Cl.
    *A61F 2/06*    (2006.01)
(52) U.S. Cl. .................................................... 623/1.15
(58) Field of Classification Search ....... 623/1.11–1.22
    See application file for complete search history.

(56) References Cited

U.S. PATENT DOCUMENTS

| 4,655,771 | A |   | 4/1987  | Wallstén |
|---|---|---|---|---|
| 4,733,665 | A |   | 3/1988  | Palmaz |
| 4,740,207 | A |   | 4/1988  | Kreamer |
| 4,776,337 | A |   | 10/1988 | Plamaz |
| 4,800,882 | A |   | 1/1989  | Gianturco |
| 4,950,227 | A |   | 8/1990  | Savin et al. |
| 4,954,126 | A |   | 9/1990  | Wallstén |
| 5,007,926 | A |   | 4/1991  | Derbyshire |
| 5,026,377 | A |   | 6/1991  | Burton et al. |
| 5,061,275 | A |   | 10/1991 | Wallstén et al. |
| 5,108,416 | A |   | 4/1992  | Ryan et al. |
| 5,122,136 | A |   | 6/1992  | Guglielmi et al. |
| 5,158,548 | A |   | 10/1992 | Lau et al. |
| 5,234,437 | A |   | 8/1993  | Sepetka |
| 5,242,399 | A |   | 9/1993  | Lau et al. |
| 5,250,071 | A |   | 10/1993 | Palermo |
| 5,261,916 | A |   | 11/1993 | Engelson |
| 5,304,195 | A |   | 4/1994  | Twyford, Jr. et al. |
| 5,312,415 | A |   | 5/1994  | Palermo |
| 5,344,426 | A |   | 9/1994  | Lau et al. |
| 5,354,295 | A |   | 10/1994 | Guglielmi et al. |
| 5,403,341 | A |   | 4/1995  | Solar |
| 5,415,664 | A |   | 5/1995  | Pinchuk |
| 5,443,500 | A | * | 8/1995  | Sigwart ..................... 623/1.17 |
| 5,453,090 | A |   | 9/1995  | Martinez et al. |
| 5,624,449 | A |   | 4/1997  | Pham et al. ................. 606/108 |
| 5,824,052 | A | * | 10/1998 | Khosravi et al. .......... 623/1.15 |
| 5,961,547 | A |   | 10/1999 | Razavi ..................... 623/1.15 |
| 5,964,797 | A |   | 10/1999 | Ho ............................. 623/1.15 |
| 5,984,929 | A |   | 11/1999 | Bashiri et al. .............. 606/108 |

(Continued)

FOREIGN PATENT DOCUMENTS

EP        707 837 A1    4/1996

(Continued)

*Primary Examiner*—Suzette J-J Gherbi
(74) *Attorney, Agent, or Firm*—Vidas, Arrett & Steinkraus, P.A.

(57) ABSTRACT

Stent and stent delivery system suited for the noninvasive treatment of aneurysms, diseased blood vessels, and other bodily lumen are described. Detachable proximal and/or distal wires connected to the proximal and distal ends, respectively, of the stent allow the operator to manipulate the position and final configuration of the stent upon deployment.

25 Claims, 2 Drawing Sheets

U.S. PATENT DOCUMENTS

| | | | |
|---|---|---|---|
| 6,007,573 A | 12/1999 | Wallace et al. | |
| 6,022,369 A * | 2/2000 | Jacobsen et al. | 606/191 |
| 6,042,597 A | 3/2000 | Kveen et al. | |
| 6,059,823 A | 5/2000 | Holman et al. | 623/1.15 |
| 6,063,101 A * | 5/2000 | Jacobsen et al. | 623/1.11 |
| 6,090,115 A | 7/2000 | Beyar et al. | |
| 6,096,034 A | 8/2000 | Kupiecki et al. | |
| 6,299,627 B1 * | 10/2001 | Eder et al. | 606/191 |
| 6,331,184 B1 * | 12/2001 | Abrams | 606/200 |
| 6,338,736 B1 * | 1/2002 | Boosfeld et al. | 606/191 |
| 6,361,558 B1 * | 3/2002 | Hieshima et al. | 623/1.16 |
| 6,416,540 B1 * | 7/2002 | Mathur | 623/1.15 |
| 6,579,308 B1 * | 6/2003 | Jansen et al. | 623/1.15 |
| 6,792,979 B1 * | 9/2004 | Konya et al. | 140/92.1 |

FOREIGN PATENT DOCUMENTS

| | | |
|---|---|---|
| WO | WO 92/02246 | 2/1992 |
| WO | WO 97/48351 | 12/1997 |
| WO | WO 00/49973 | 8/2000 |

* cited by examiner

STENT DEVICES WITH DETACHABLE DISTAL OR PROXIMAL WIRES

This application is a continuation of patent application Ser. No. 09/724,731 filed Nov. 28, 2000 now U.S. Pat. No. 6,579,308, from which priority is claimed under 35 USC §120, and which is incorporated herein by reference in its entirety.

FIELD OF THE INVENTION

This invention is a stent and stent delivery system suited for the noninvasive treatment of aneurysms, diseased blood vessels, and other bodily lumen. Unlike most known stents, the stents described herein are able to be positioned in situ with one or more wires attached to at least one location at the distal end of the stent and/or at least one location at the proximal end of the stent.

BACKGROUND

This invention is an stent and stent delivery system which may be used within various portions of the body's vasculature. In general, stents are prosthetic devices which may be introduced into a body cavity such as the lumen of a blood vessel or in some other difficult to access location. Stents are particularly useful for permanently widening a vessel which is either in a narrowed condition or has been damaged by aneurysm. Stents are typically introduced into the vasculature or other body cavity by the use of a catheter. Stents are usually tubular bodies made up of radially stiff shapes (for example circles) connected together to form the tubular shape.

Currently, the majority of stents are delivered to the target site as radially expandable preformed structures. In other words, only the diameter of the stent may be increased or decreased once properly positioned in the region where they are to be left. For instance, WO 92/02,246, owned by Numed, Inc., shows a radially expandable stent made from fine wire formed into a serpentine ribbon wound into a cylindrical shape for introduction into a body vessel. The stent is placed within the vessel over a balloon which, when expanded, expands the stent in a radial fashion to support the wall of the vessel in the expanded configuration. This stent is said to be useful in the transluminar implantation of a stent for use in coronary angioplasty to prevent restenosis.

Other disclosures of expandable intraluminal stents involving radially expanding wire mesh include U.S. Pat. No. 4,776,337, to Palmaz. The patent shows a tubular member which may be made of a variety of different things supported by a gridlike collection of metal or plastic wires. U.S. Pat. No. 4,800,882, to Gianturco, shows a wire stent made of a number of curved sections that are formed into a generally circular configuration. U.S. Pat. No. 6,007,573 shows a rolled sheet stent releasably mounted on the distal tip of the deployment catheter. U.S. Pat. No. 06,063,101 shows a balloon expandable stent which includes a hollow wire through which drugs and the like are delivered to the stent itself. The hollow wire is detached after drug deliver using ultrasonic energy.

Stents delivered to a restricted coronary artery, expanded to a larger diameter as by a balloon catheter, and left in place in the artery at the site of a dilated lesion are shown in U.S. Pat. No. 4,740,207 to Kreamer; U.S. Pat. No. 5,007,926 to Derbyshire; U.S. Pat. No. 4,733,665 to Palmaz; U.S. Pat. No. 5,026,377 to Burton et al.; U.S. Pat. No. 5,158,548 to Lau et al.; U.S. Pat. No. 5,242,399 to Lau et al.; U.S. Pat. No. 5,344,426 to Lau et al.; U.S. Pat. No. 5,415,664 to Pinchuk; U.S. Pat. No. 5,453,090 to Martinez et al.; U.S. Pat. No. 4,950,227 to Savin; U.S. Pat. No. 5,403,341 to Solar; U.S. Pat. No. 5,108,416 to Ryan et al. and European Patent Application No. 707 837 A1 to Sheiban, all of which are incorporated herein by reference.

WO 97/48351, to the Medical University of South Carolina, discloses a multiple layered, self-forming intravascular flow modifier (IFM). Notably, at least a portion of the outer layer surrounds at least a portion of the inner layer so that at least some loops of the outer layer overlap and contact at least some loops of the inner layer. In other words, the turns making up the final configuration are necessarily overlapping and touching each other. The IFM also has a relatively high stiffness. The IFM is deployed using co-axial catheters.

None of these documents depict self-expandable or self-forming stents having a wire attached to the proximal end of the stent and/or the distal end of the stent which allow the operator to position the stent in situ. Further, none describe a self-forming stent which forms a tubular structure of turns from a substantially linear configuration upon deployment and in which the turns making up the tubular structure do not contact each other. Thus, the present invention is particularly directed to stents which can be configured upon deployment and delivery systems which facilitate delivery thereof.

SUMMARY OF THE INVENTION

Thus, this invention includes novel stents, stent delivery systems and methods of using these stents and stent delivery systems.

In one aspect, the invention includes a self-expandable and self-forming stent device having a proximal end and a distal end and at least one detachable proximal wire connected to the proximal end or at least one detachable distal wire connected to the distal end. The stents can comprise at least one detachable proximal wire connected to the proximal end of the stent; at least one distal wire connected to the distal end of the stent; or both at least one proximal and at least one distal wire connected to the proximal and distal ends of the stent, respectively. In some embodiments, the proximal and/or distal wires are attached to more than one location of the stent. In some embodiments, one or more of the attached distal and/or proximal wires are electrolytically detachable from the stent by imposition of a current on the proximal wire. In other embodiments, one or more of the attached distal and/or proximal wires are adapted to detach from the stent using mechanical, hydraulic, ultrasonic or radio-frequency detachment mechanisms. In yet other embodiments, the stent further comprises at least one insulator between the proximal and distal wires. In other embodiments, any of the stent described herein further comprise at least one aperture through which the distal wire is threaded. Further, any of the stents described herein can further comprise a bioactive coating (e.g., a therapeutic agent). In still further embodiments, any of the stent devices described herein further comprise a sheath. The sheath can further include at least one delivery wire.

In other aspects, stents with attached proximal and/or distal wires are self-forming. In some embodiments, the self-forming stent device has a first substantially linear configuration for insertion into a restraining member and a second tubular configuration upon extrusion from the restraining member, the second tubular configuration comprising a plurality of turns, wherein the turns are not touching and further wherein the second tubular configuration has an outer diameter and at least a portion of the outer diameter conforms to the vasculature. In certain embodiments, the stent self-forms into the second tubular configuration and the restraining member comprises a deployment catheter. In other embodiments, the stent further includes at least one aperture in each turn of the secondary configuration through which the distal wire is threaded.

In other aspects, the invention includes a method of delivering any of the self-forming stents described herein to a selected site in a body cavity, the method comprising: (a) loading a substantially straightened, self-forming stent into a catheter; (b) accessing the selected site with the catheter; and (c) discharging the stent from the catheter at the selected site, wherein the stent forms a tubular configuration upon discharge. In certain embodiments, wherein step (c) comprises: (i) pushing the stent out of the catheter by applying pressure to the proximal wire while keeping the stent in the desired location by applying tension to the distal wire; and (ii) applying electrical impulses sufficient to detach the distal and proximal wires from the stent. In addition, step (c) further comprises (iii) moving the catheter. In some embodiments, the selected site is a lesion.

These and other embodiments of the subject invention will readily occur to those of skill in the art in light of the disclosure herein.

DESCRIPTION OF THE INVENTION

Figure 1:
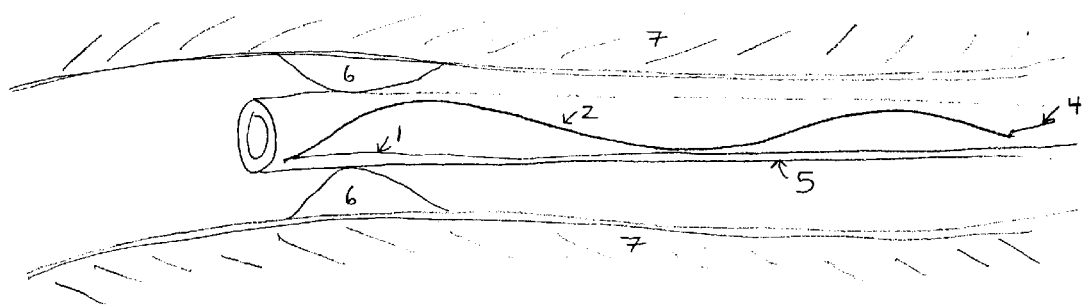
FIG. 1 depicts a step in deployment of an exemplary stent of the present invention. The stent is depicted within a deployment catheter. Also shown are a proximal wire attached via an electrolytically detachable mechanism to the proximal end of the stent and a distal wire attached via an electrolytically detachable mechanism to the distal end of the stent.

The present invention includes self-forming or self-expandable stent devices comprising one or more distal wires and/or one or more proximal wires detachably connected to the ends of the stent device. The wires allow the operator to manipulate the position and final configuration of the stent upon deployment. Stent delivery systems (e.g, including inventive stents described herein including proximal and distal wires and a catheter) and methods of using the stents and stent delivery systems are also included in the present invention.

In one aspect, the stent comprises a self-expandable stent device with attached proximal and/or distal wires. Self-expandable stents are, as described, for example, in U.S. Pat. No. 6,042,597; U.S. Pat. No. 4,655,771 to Wallensten, U.S. Pat. No. 4,954,126 to Wallensten and U.S. Pat. No. 5,061,275 to Wallensten et al. and references cited therein. Thus, in some embodiments the stent with attached delivery wires does not require a balloon or other external application of force to expand, but, rather, self-expand longitudinally and/or radially or upon deployment.

In other aspects, the stent with attached proximal and/or distal wires comprises a self-forming stent which does not assume its final tubular configuration until deployed at the target site. Thus, in these embodiments, the stent is pre-formed into a tubular configuration but delivered to the target site in a substantially straightened (e.g., linear yet flexible) configuration, for example within a restraining member such as a catheter. Upon extrusion from the deployment catheter, the stent forms a coiled, tubular configuration in which the individual turns of the coil are not touching each other. The stent is pre-formed into the final tubular structure, for example by winding an elongated wire into a helical coil. The stent can then be substantially straightened for introduction into a catheter and does not form the final tubular configuration until deployment.

In yet other aspects, the self-forming or expandable stents of the invention further include a sheath or covering which accompanies the stent as it is moved within the deployment catheter. The sheath is preferably flexible and/or lubricated, for example treated with a low friction polymer that allows easy movement within the catheter. Further, one or more wires attached to sheath allow for removal of the covering upon placement of the stent in the desired position. Further, stent delivery systems can be prepackaged with stent, sheath and attached wires.

Advantages of the present invention include, but are not limited to, (i) providing stent devices whose outer diameter conforms to the vasculature of the target site; (ii) enhancing the ability to place stents in small, tortuous vessels; (iii) providing greater control of the positioning of the stent during deployment; (iv) providing greater control of the configuration of stent during deployment; and (v) facilitating deployment by providing self-forming stent devices that are in a substantially linear shape during deployment.

All publications, patents and patent applications cited herein, whether supra or infra, are hereby incorporated by reference in their entirety.

It must be noted that, as used in this specification and the appended claims, the singular forms "a", "an", and "the" include plural referents unless the content clearly dictates otherwise. Thus, for example, reference to "a wire" includes two or more.

The most common noninvasive therapy for aneurysms is through the process of filling the aneurysm sac with one of a variety of fillers such as detachable expandable microballoons and coils. Each of these procedures, however, require the placement of the material into the aneurysm sac via the neck of the aneurysm. These methods therefore run the substantial risk of rupturing the wall of the sac and causing severe hemorrhaging. Obviously, this is especially true if the wall of the aneurysm is extremely thin. The amount of material necessary to fill the aneurysm completely is often difficult to determine. Use of too large an amount may result in migration of the introduced material into other segments of the vasculature thereby causing the production of emboli or vessel blockage.

Many aneurysms occur in tortuous segments of the vasculature. Access to aneurysm sites can be extremely difficult. The inflexibility of most pre-formed metallic stents is also likely to damage the endothelial wall of healthy arteries during delivery. Finally, it is unlikely that the blood vessel from which the aneurysm arises is straight in the region of the aneurysm. Therefore, a stent should exhibit some flexibility along its axis so to conform to the curvature of the vessel at the aneurysm site. Furthermore, it is difficult to position most stent devices after or during deployment.

Accordingly, the stents described herein are able to be positioned at the target site during deployment by the operator using detachably connected distal and/or proximal wires. It will be apparent from the teachings herein that the stents can include one or more proximal wires; one or more distal wires; or one or more distal and proximal wires. Furthermore, the proximal and distal wires can be connected, via a detachable mechanism, at multiple locations on the stent.

Shown in FIG. 1 is a self-forming stent with detachable distal 1 and proximal 4 wires. These wires may be made of any suitable material or combinations of material. Preferably, the wires are made of an electro-conductive material such as nitinol (or other super-elastic alloy), stainless steel or a cobalt alloy. The wire may be of the same material as the stent or made of different material.

The distal wire is attached to, at least, the distal end of the stent while the proximal wire is attached to, at least, the proximal end of the end. In both self-expanding and self-forming stents, both the proximal and/or distal wires can be used to push and pull the stent device as desired by the operator. By way of example only, in certain instances, the flexibility needed to allow a self-forming stent to conform to the vasculature may impede self-formation. Accordingly, the distal wire is especially useful in these instances as it imparts the ability to configure the secondary, tubular structure by exerting tension as the stent is extruded from the catheter.

The proximal and distal wires are attached to the stents described herein via any suitable attachment mechanism that can be readily detached by an operator. For example, a variety mechanically detachable mechanisms are described in, for example, U.S. Pat. No. 5,234,437, to Sepetka, U.S. Pat. Nos. 5,250,071 and 5,312,415, to Palermo, U.S. Pat. No. 5,261,916, to Engelson, and U.S. Pat. No. 5,304,195, to Twyford et al.). Other mechanical type detachable mechanisms include screw-type connections, hydraulically detachable connections and the like. Mechanism that are detached using electrolytic, ultrasonic and/or radio-frequency methods also form an aspect of the invention.

In certain embodiments, the detachment junction is electrolytically detachable. U.S. Pat. No. 5,354,295 and its parent, U.S. Pat. No. 5,122,136, both to Guglielmi et al., describe an electrolytically detachable mechanism. As disclosed therein, in these embodiments, the stent is bonded via a metal-to-metal joint to the proximal wire and distal wire. Furthermore, the stent preferably includes at least one insulator between the proximal and distal wire attachment sites so that the operator can detach each wire separately if desired. The stent is deployed from the catheter to the target site and a small electrical current is passed through the proximal/distal wire-stent assembly. The current causes the joint between the proximal or distal wire and the stent to be severed via electrolysis. The proximal wire, distal wire and catheter may then be retracted leaving the detached stent at an exact position within the vessel. Since no significant mechanical force is applied to the stent during electrolytic detachment, highly accurate placement is readily achieved. The proximal wire 4 can be controlled by an operator to push segments of the stent making up the individual turns of the stent into the vasculature. At the same time, the operator can control the tension on the distal wire 1 to control positioning of the distal end of the stent. Thus, the proximal and distal wires are detachably attached to the stent, for example via electrolytically detachment mechanisms.

The proximal and/or distal wires may contact multiple locations on the stent. Thus, in certain embodiments, the distal wire is detachably connected to one location and the distal end of the stent and one or more additional locations on the stent. If physically connected, each attachment junction is readily detachable.

Figure 4:
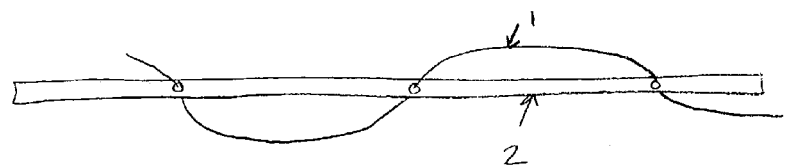
FIG. 4 depicts a substantially straightened exemplary stent according to the present invention wherein the distal wire is threaded through apertures (holes) in the wire making up the stent and attached to the distal end of the stent.

As shown in FIG. 4, in yet other embodiments, the distal wire 1 is threaded through the a hole in the wire(s) making up the stent 2 at one or more turns of the preformed helical structure, further adding to the operator's ability to control position during deployment. When the stent is positioned at the desired target site, the operator detaches the end of the distal wire and pulls it back through the holes to remove it from the subject.

The stents described herein are typically pre-shaped or pre-formed. For example, for the self-forming embodiments, a helical coil is shaped from a flexible material, for example a flexible metallic wire. Methods of forming such coil structures are known in the art, for example by winding an elongated wire around a mandrel. The stent can be straightened into a first, substantially linear configuration for insertion into a deployment mechanism (e.g., catheter) and self-forms to some extent into a second tubular configuration upon deployment at the target site.

The self-expandable and self-forming stent devices of the invention are preferably constructed of material having sufficient softness and resilience to allow formation of a tubular structure whose outer diameter conforms essentially to the diameter of the vasculature. In other words, the diameter of the tubular configuration varies across the length of the stent such that the outer portion of one or more turns is contact with the vasculature. In certain instances, the softness of a self-forming stent may somewhat impede self-formation of the second, tubular configuration. In these instances, the self-forming stent can be configured into the desired location and dimensions using the distal wire attached to the distal end of the stent and/or a proximal wire attached to the proximal end of the stent. Positioning and formation of a self-forming stent can also be controlled to some extent by manipulating the deployment catheter, for example, withdrawing at a rate such that one stent turn (e.g., individual turn of the coil) is deployed at a time. Accordingly, each turn of the stent's tubular configuration can be positioned and formed while the distal end of the stent is kept in place using the distal wire and the catheter and proximal wire are manipulated by the operator.

The second, tubular configuration of the deployed stents described herein are typically comprised of a plurality of helical turns. The pitch, spacing and diameter of each turn can be varied according to preference. In addition, the overall tube shape of the stent may be achieved using a variety of shapes (e.g., circles, ovals, etc). Each turn need not have the same pitch, diameter or shape as the other turns.

When the stent comprises a self-forming type, the stent is configured (e.g, softness and lack of contact and/or permanent and/or temporary physical connection between the turns) such that it can be straightened substantially for insertion into a deployment catheter yet still self-form into a tubular structure upon deployment. It will also be apparent from the teachings herein that the pre-formed tubular shape of the inventive stents need not be completely linear within the deployment catheter.

It is known that certain vaso-occlusive coils are secured in the vasculature if contact is maintained between the vasculature and coil for a sufficient amount of time (see, e.g., co-owned U.S. Pat. No. 6,096,034). Similarly, the inventive stents described herein can be secured within the vasculature if the contact between the turns of the stent and vasculature is maintained for a sufficient amount of time. Determining the appropriate amount of time will depend on factors, for example, stent material, size of vasculature, size of lesion, maintenance of long term clinical objective (e.g., maintaining stent inner diameter and integrity). One of skill in the art can readily determine such time in view of the teachings and references cited herein. Typically, the stent will be secured if held in placed between about 2 seconds to about 2 minutes, more preferably less than about one minute.

The material used in constructing the stents described herein may be any of a wide variety of materials; preferably, the proximal and distal ends of the stent include sufficient amounts of one or more electrically conductive materials to allow for electrolytically detachable linkages to the proximal and distal wires. Preferably, the stent also includes a radio-opaque material (e.g., a metal). Suitable metals and alloys for the wire making up the stent include the Platinum Group metals, especially platinum, rhodium, palladium, rhenium, as well as tungsten, gold, silver, tantalum, and alloys of these metals. These metals have significant radiopacity and in their alloys may be tailored to accomplish an appropriate blend of flexibility and stiffness. They are also largely biologically inert. Highly preferred is a platinum/tungsten alloy.

The stent may also be of any of a wide variety of stainless steels if some sacrifice of radiopacity may be tolerated. Certain "super-elastic alloys" include nickel/titanium alloys (48–58 atomic % nickel and optionally containing modest amounts of iron); copper/zinc alloys (38–42 weight % zinc); copper/zinc alloys containing 1–10 weight % of beryllium, silicon, tin, aluminum, or gallium; or nickel/aluminum alloys (36–38 atomic % aluminum). Particularly preferred are the alloys described in U.S. Pat. Nos. 3,174,851; 3,351,463; and 3,753,700. Especially preferred is the titanium/nickel alloy known as "nitinol". These are very sturdy alloys which will tolerate significant flexing even when used as a very small diameter.

Generally speaking, when the stents are formed of a metallic material and that metal is a platinum alloy or a superelastic alloy such as nitinol, the diameter of a single wire used to make the stent will be in the range of 0.001 and 0.05 inches. Similarly, if the stents are formed from a wire which is then wound with a radioopaque material, the diameter of the wire is preferably in the range of 0.001 to 0.02 inches. The wire of such diameter is typically then formed into a stent having a primary diameter of between 0.005 and 0.035 inches. For most neurovascular indications, the preferable diameter is 0.010 to 0.018 inches. The wire is typically of sufficient diameter to provide a hoop strength to the resulting device sufficient to hold the device in place within the chosen body cavity without distending the wall of the cavity and without moving from the cavity as a result of the repetitive fluid pulsing found in the vascular system. The overall diameter of the device as deployed is generally between 2 and 30 millimeters. Thus, all of the dimensions here are provided only as guidelines and are not critical to the invention. However, only dimensions suitable for placement within the human body are included in the scope of this invention.

The stents described herein can also include additional additives, for example, any material that exhibits biological activity in vivo, for example, including but not limited to, therapeutic agents such as taxol. Non-limiting examples of suitable bioactive materials are known to those of skill in the art and described in the art.

In addition one or more metals, the stents may optionally include a wide variety of synthetic and natural polymers, such as polyurethanes (including copolymers with soft segments containing esters, ethers and carbonates), ethers, acrylates (including cyanoacrylates), olefins (including polymers and copolymers of ethylene, propylene, butenes, butadiene, styrene, and thermoplastic olefin elastomers), polydimethyl siloxane-based polymers, polyethyleneterephthalate, cross-linked polymers, non-cross linked polymers, rayon, cellulose, cellulose derivatives such nitrocellulose, natural rubbers, polyesters such as lactides, glycolides, caprolactones and their copolymers and acid derivatives, hydroxybutyrate and polyhydroxyvalerate and their copolymers, polyether esters such as polydioxinone, anhydrides such as polymers and copolymers of sebacic acid, hexadecandioic acid and other diacids, orthoesters may be used. In a preferred embodiment, the polymeric filament comprises the materials of the present invention or other suture materials that have already been approved for use in wound heating in humans.

Polymeric materials which are activatable can also be included, for example thioisocyanates, aldehydes, isocyanates, divinyl compounds, epoxides or acrylates. In addition to the aforementioned, photoactivatable crosslinkable groups as succinimidyl azido salicylate, succinimidyl-azi-dobenzoate, succinimidyl dithio acetate, azidoiodobenzene, fluoro nitrophenylazide, salicylate azides, benzophenone-maleimide, and the like may be used as photoactivatable crosslinking reagents. The activatable material may also consist of a thin coating which can be activated by external forces such as laser, radio-frequency, ultrasound or the like, with the same hardening result taking place. These materials would allow for normal tissue ingrowth to take place.

In other embodiments, the self-forming or expandable stents described herein further include a sheath or covering. The sheath may serve a variety of purposes, for example, to constrain self-expanding stents or to easy delivery, for example by providing a lubricated sheath. Methods of increasing lubricity are known in the art, e.g., using a sheath comprising a low friction polymer. Preferably, the sheath also has one or more delivery wires attached thereto. In this way, the stent can be delivered easily through a catheter while within the sheath. The sheath delivery wires could then be used to. unsheath the stent while the proximal and/or distal wires of the stent are used to keep it in the desired position. This allows for very precise placement of the stent and reduced or eliminates jumping. The proximal and/or distal wire(s) of the stent can then be detached as described above.

Stent Delivery Systems and Methods of Use

The present invention also includes stent delivery systems (e.g., stent, proximal wire, distal wire, sheath, catheter and/or guidewire) and methods of using the stents described herein. The stents described herein are preferably introduced to the chosen site using the procedure outlined below. This procedure may be used in treating a variety of maladies. In some embodiments, the stent is used alone, for example, as shown in the accompanying FIGS to assist in facilitating blood flow near a site of injury in the vasculature. In other embodiments, the stent is used in combination with one or more additional devices. For instance, in treatment of an aneurysm, the aneurysm itself may be filled with the mechanical devices prior to introducing the inventive stent.

Shortly after these mechanical vaso-occlusive devices are placed within the aneurysm, an emboli begins to form and, at some later time, is at least partially replaced by neovascularized collagenous material formed around the vaso-occlusive devices. The stent then serves to hold open the vasculature around the emboli.

In using the stent, a selected site is reached through the vascular system using a collection of specifically chosen catheters and guide wires. Accordingly, the stents described herein are typically first loaded into a carrier, for example a delivery catheter, for introduction into the body cavity and delivery to the target site. It is clear that should the target site be in a remote site, e.g., in the brain, methods of reaching this site are somewhat limited. One widely accepted procedure is found in U.S. Pat. No. 4,994,069 to Ritchart, et al. It utilizes a fine endovascular catheter such as is found in U.S. Pat. No. 4,739,768, to Engelson. First of all, a large catheter is introduced through an entry site in the vasculature. Typically, this would be through a femoral artery in the groin. Other entry sites sometimes chosen are found in the neck and are in general well known by physicians who practice this type of medicine. Once the introducer is in place, a guiding catheter is then used to provide a safe passageway from the entry site to a region near the site to be treated. For instance, in treating a site in the human brain, a guiding catheter would be chosen which would extend from the entry site at the femoral artery, up through the large arteries extending to the heart, around the heart through the aortic arch, and downstream through one of the arteries extending from the upper side of the aorta. A guidewire and neurovascular catheter such as that described in the Engelson patent are then placed through the guiding catheter as a unit. Once the tip of the guidewire reaches the end of the guiding catheter, it is then extended using fluoroscopy, by the physician to the site to be treated using the vaso-occlusive devices of this invention. During the trip between the treatment site and the guide catheter tip, the guidewire is advanced for a distance and the neurovascular catheter follows. Once both the distal tip of the neurovascular catheter and the guidewire have reached the treatment site, and the distal tip of that catheter is appropriately situated, e.g., within the vasculature to be treated, the guidewire is then withdrawn. The neurovascular catheter then has an open lumen to the outside of the body. The devices of this invention are then deployed into the vasculature.

Referring to the drawings in detail, wherein like numerals indicate like elements, exemplary deployment of a self-forming type stent as described herein is depicted. The operation of the assembly generally comprises the steps of (1) advancing a catheter through a vessel lumen, for example, to the vicinity of the site to be occluded (e.g., an aneurysm, vascular malformation, or arterial venous fistula), (2) advancing the substantially linearized tubular stent through the catheter to the target location, and (3) pushing or pulling the stent using the proximal and distal wires and/or moving the catheter to deploy the stent into the target site in a tubular configuration.

Referring to FIG. 1, a self-forming stent 2 is dimensioned to be able to be advanced through a catheter 5 that is sized to access the desired site, in particular using a sufficiently soft material to allow straightening. Further, the turns making up the helical, tubular shape of the stent as deployed are not touching. In addition, the turns are not connected, so that the stent can be substantially straightened (rather than simply radially constricted) for insertion into a deployment catheter. The attached distal wire provides the ability to position the stent without sacrificing the softness which allows the stent to conform its outer diameter to that of the target site vasculature. Distal wire 1 is shown attached to the distal end of the stent 2, via a remotely detachable mechanism (e.g., GDC-type electrolytic detachment mechanism). Proximal wire 4 is shown attached to the proximal end of the stent 2, also via a remotely detachable mechanism. The stent-containing catheter 5 is positioned within the vasculature 7 across the target lesion 6.

The catheter 5 is suitable for delivering the stent 2 and transmitting electrical impulses to electrolytically detach the proximal wire 4 and the distal wire 1 from the stent 2. The catheter 5 is inserted through the vessel lumen to the target site (e.g., an aneurysm, lesion, etc.). Conventional catheter insertion and navigational procedures involving guidewire and/or flow-directed means may be used to access the site with the catheter. Thus, although not shown, catheter 5 may include a guidewire usable therewith to guide the distal end of the catheter toward the desired or selected occlusion site. Guidewires of this type are commercially available, and generally include an elongate wire having a tapered, wire-wound distal end region which is adapted to be advanced through a tortuous vessel path, with the catheter being moved axially along the advanced guidewire.

The catheter is preferably between about 50–300 cm in length, and typically between about 60–200 cm in length. The catheter also is designed for accessing a vessel site at which, for example, the stent is desired. For example, the vessel site may be within a small diameter vessel 46 having 2–5 mm lumen diameter and accessible by way of a tortuous vessel path which may involve sharp vessel turns and multiple vessel branches. In that case, the catheter preferably has a small diameter, flexible construction with a lumen diameter of less than about 40 mil, and preferably between about 8–30 mil. Catheters of this type, which are typically used for accessing deep brain vascular sites, are commercially available.

Figure 2:
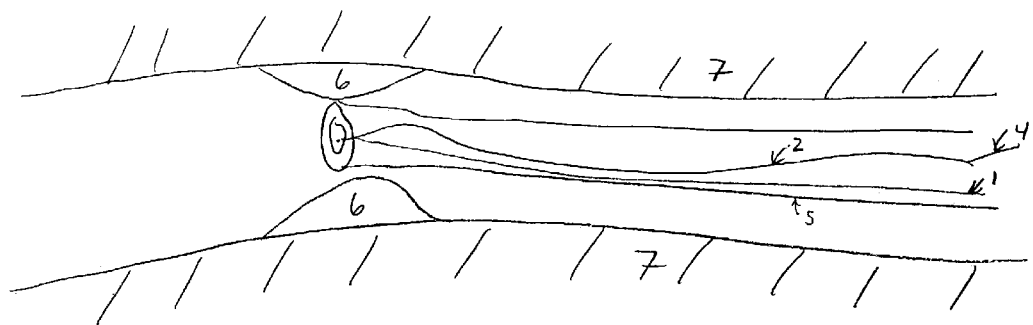
FIG. 2 depicts the stent delivery system of FIG. 1 in which an operator has pulled the catheter back and pushed the stent out of the catheter with the proximal wire. The stent is maintained in the desired location over the lesion by exerting tension on the distal wire.

Referring to FIG. 2, once the distal end of the self-forming stent is positioned at the selected site as depicted in FIG. 1 (e.g. its location may be determined by a coating at the distal end of the catheter with a radiopaque material or otherwise affixing such a material to the distal end of the catheter or incorporating such a material into the distal end of the catheter), the catheter 5, proximal wire 4 and distal wire 1 are manipulated to deploy the stent 2 from the catheter. Upon deployment, the stent assumes a pre-formed helical shape. In particular, the catheter 5 is pulled back slightly and the proximal wire 4 used to push the stent 2 out of the catheter. At the same time, the operator controls the tension on the distal wire 1 to keep the distal end of the stent 2 in place, for example perpendicular to the vasculature 7.

Figure 3:
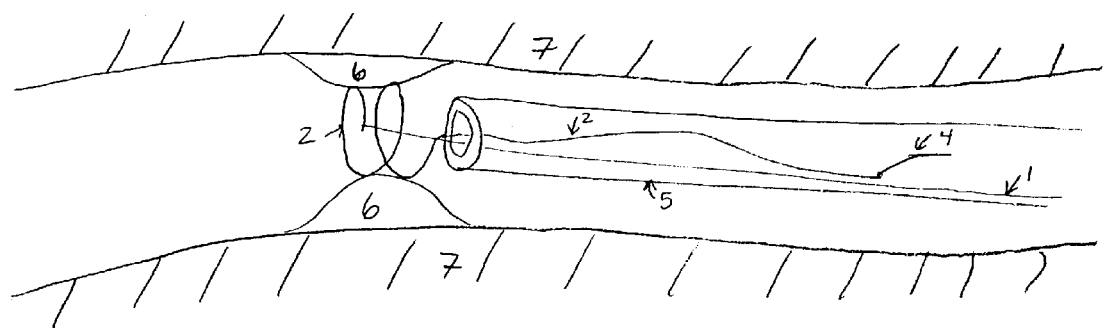
FIG. 3 depicts the stent delivery system of FIGS. 1 and 2 in which the operator has pulled the catheter farther back and pushed the stent farther out of the catheter with the proximal wire while exerting tension on the distal wire. The stent which has been deployed from the catheter is a tubular coil configuration.

FIG. 3 depicts further deployment of the stent 2 across the lesion 6 as shown in FIGS. 1 and 2. In FIG. 3, the stent 2 is shown forming its final tubular (e.g., helical coil) configuration upon discharge from the catheter 5. The catheter 5 is pulled slightly farther back and the proximal wire 4 used to push more of the stent 2 out of the catheter 5. Again, the tension on the distal wire 1 is controlled to keep the stent 2 in place. The manipulations of catheter 5, proximal wire 4, and distal wire 1 are repeated until the stent 2 is placed in the desired location in the vasculature 7.

In other embodiments, the stents described herein may include a sheath with one or more attached wires. In these embodiments, the stents can be positioned using the distal and proximal wires and, moreover, held in position while the sheath is removed using the wire attached thereto.

The stents and stent delivery systems may be used as a kit with other implantable devices.

Modifications of the procedure and device described above, and the methods of using them in keeping with this invention will be apparent to those having skill in this mechanical and surgical art. These variations are intended to be within the scope of the claims that follow.

What is claimed is:

1. A stent device having a proximal end and a distal end and at least one detachable distal wire connected to the distal end, wherein the detachable distal wire comprises an electrolytically detachable end adapted to detach from the stent by imposition of a current on the distal wire.

2. The stent device of claim 1, comprising at least one detachable proximal wire connected to the proximal end.

3. The stent of claim 2, wherein the detachable proximal wire comprises an electrolytically detachable end adapted to detach from the stent by imposition of a current on the proximal wire.

4. The stent of claim 2, wherein the detachable proximal wire is adapted to detach from the stent using mechanical, hydraulic, ultrasonic or radio-frequency detachment mechanisms.

5. The stent of claim 2, wherein the distal and proximal wires are each further attached to least one additional site in the stent.

6. The stent of claim 5, wherein the stent further comprises at least one insulator between the sites of attachment of the proximal wire and the sites of attachment of the distal wire.

7. The stent of claim 5, wherein each additional site of attachment is via an electrolytically detachable link.

8. The stent of claim 5, wherein the each additional site of attachment is via mechanical, hydraulic, ultrasonic or radio-frequency detachable link.

9. The stent of claim 1, further comprising at least one insulator between the proximal and distal ends.

10. The stent of claim 1, wherein the distal wire is further attached to at least one additional location in the stent.

11. The stent of claim 1, further comprising at least one aperture through which the distal wire is threaded.

12. The stent of claim 1, further comprising a bioactive coating.

13. The stent of claim 12, wherein the bioactive coating comprises a therapeutic agent.

14. The stent device of claim 1, wherein the stent is self-expandable.

15. The stent device of claim 1, wherein the stent is self-forming.

16. The stent device of claim 15, wherein the stent has a first substantially linear configuration for insertion into a restraining member and a second tubular configuration upon extrusion from the restraining member, the second tubular configuration comprising a plurality of turns, wherein the turns are not touching and further wherein the second tubular configuration has an outer diameter and at least a portion of the outer diameter conforms to the vasculature.

17. The stent of claim 16, wherein the stent self-forms into the second tubular configuration.

18. The stent of claim 16, wherein the restraining member comprises a deployment catheter.

19. The stent of claim 16, wherein the stent further includes at least one aperture in each turn of the secondary configuration through which the distal wire is threaded.

20. A method of delivering a stent according to claim 16 to a selected site in a body cavity, the method comprising:
(a) loading a substantially straightened stent according to claim 16 into a catheter;
(b) accessing the selected site with the catheter; and
(c) discharging the stent from the catheter at the selected site, wherein the stent forms a tubular configuration upon discharge.

21. The method of claim 20, wherein step (c) comprises:
(i) pushing the stat out of the catheter by applying pressure to the proximal wire while keeping the stent in the desired location by applying tension to the distal wire; and
(ii) applying electrical impulses sufficient to detach the distal and proximal wires from the stent.

22. The method of claim 21, wherein step (e) further comprises:
(iii) moving the catheter.

23. The method of claim 20, wherein the selected site is a lesion.

24. The stent device of claim 1, further comprising a sheath.

25. The stent of claim 24, wherein the sheath further includes at least one delivery wire.

* * * * *